(12) United States Patent
Garth et al.

(10) Patent No.: US 7,101,348 B2
(45) Date of Patent: Sep. 5, 2006

(54) LUMBAR SUPPORT WITH SUPPLEMENTAL ABDOMINAL SUPPORT PANELS

(75) Inventors: Geoffrey Garth, Long Beach, CA (US); Albert Romo, Long Beach, CA (US)

(73) Assignee: Carsar, LLC, Seal Beach, CA (US)

( * ) Notice: Subject to any disclaimer, the term of this patent is extended or adjusted under 35 U.S.C. 154(b) by 0 days.

(21) Appl. No.: 10/971,205

(22) Filed: Oct. 22, 2004

(65) Prior Publication Data

US 2006/0086355 A1 Apr. 27, 2006

(51) Int. Cl.
*A61F 5/00* (2006.01)
(52) U.S. Cl. .............................. 602/19; 128/845; 2/44
(58) Field of Classification Search ............ 602/19–20, 602/32–38, 60–61, 67; 128/101.1, 112.1, 128/95.1, 96.1, 100.1; 2/44, 45, 908, 92, 2/445; 450/117–118, 120, 122–126, 130, 450/131, 146, 150, 114, 115; D2/625, 702
See application file for complete search history.

(56) References Cited

U.S. PATENT DOCUMENTS

| | | | |
|---|---|---|---|
| 4,108,149 A | * | 8/1978 | Castiglia ..................... 450/155 |
| 4,557,268 A | | 12/1985 | Maddux |
| 4,952,192 A | | 8/1990 | Burke |
| 5,060,639 A | | 10/1991 | Marcus |
| 5,094,648 A | | 3/1992 | Turner |
| 5,445,601 A | * | 8/1995 | Harlow ......................... 602/19 |
| D374,547 S | * | 10/1996 | McDonald et al. ..... D29/101.3 |
| 5,690,609 A | * | 11/1997 | Heinze, III ................... 602/19 |
| 6,071,175 A | | 6/2000 | Working |
| 6,102,879 A | * | 8/2000 | Christensen et al. .......... 602/19 |
| 6,213,968 B1 | * | 4/2001 | Heinz et al. .................. 602/19 |
| 6,503,215 B1 | * | 1/2003 | Reinhardt et al. ............ 602/19 |
| 6,676,620 B1 | * | 1/2004 | Schwenn et al. ............. 602/12 |

* cited by examiner

*Primary Examiner*—Henry Bennett
*Assistant Examiner*—Shumaya B. Ali
(74) *Attorney, Agent, or Firm*—Rutan & Tucker, LLP

(57) ABSTRACT

A lower torso support has first and second front panels that are attachable to each other and independently moveable with respect to the side portions of the support. The front panels can be any suitable dimensions. However, slipper shapes are deemed to be the most useful, with front panels preferably at least 15 cm long and at least 6 cm tall at their tallest point. In preferred embodiments the front panels are readily attachable to and detachable from the side portions in a wide variety of superior to inferior and medial to lateral positions. At present the preferred mechanism for making those connections is a hook and loop mechanism, which has the advantage of also allowing the front panels to be angled with respect to the side portions in any suitable orientation.

20 Claims, 2 Drawing Sheets

LUMBAR SUPPORT WITH SUPPLEMENTAL ABDOMINAL SUPPORT PANELS

FIELD OF THE INVENTION

The field of the invention is lower torso (lumbar and abdominal) supports.

BACKGROUND

The added abdominal weight attending mid to late pregnancy, obesity, ascites, and various other conditions can produce significant lumbar back strain. In some cases a standard lumbar brace can provide significant assistance to the wearer, but in other cases (such as pregnancy) the ordinary lumbar braces are much too compressive on the peritoneum.

U.S. Pat. No. 5,094,648 to Turner (March 1992) shows one type of pregnancy support, in which a fabric encircles the torso, but remains open about the abdominal region so as not to compress the abdomen. This and all other referenced patents and applications are incorporated herein by reference in their entirety. While providing some measure of back support, devices such as that disclosed in the '648 patent do little or nothing to support the abdomen, or transfer abdominal weight onto the hips.

U.S. Pat. No. 6,071,175 to Loren Working (Jun. 6, 2000) teaches a supports designed specifically for pregnant women. That support provides a continuous carrier about the wearer's lower torso, with a front portion that is shorter (from bottom to top) than the sides and back, so that the front portion supports the extended lower abdomen substantially from below the extended abdomen. This arrangement provides needed support without excessive compression of the abdomen. The '175 patent also teaches a removable apron band that is said to facilitate installation and proper positioning of the front (natal support) portion.

Unfortunately, supports according to the '175 patent are not readily adjustable. One problem is that the back and side portions of the support are fixedly coupled to the front portion. Whether in pregnancy or other conditions, abdominal distension may occur high or low relative to the lumbar spine, and the positioning and extent of the distension commonly varies over time. The result is that proper fitting of the back and side portions of the support is often inconsistent with proper fitting of the front portion, and visa versa. It is possible to resolve that problem by producing a large number of different sizes, but that solution adds considerably to the manufacturing and stocking costs, as well as requiring a wearer to purchase multiple supports.

U.S. Pat. No. 5,060,639 to Marcus (October 1991) teaches a torso support comprising a back pad, side pads, and upper and lower front straps. The '639 device is advantageous in that the front straps are positioned above and below the most fully distended portion of the abdomen, but still cannot be positioned independently of the positioning of the back and side pads.

U.S. Pat. No. 4,952,192 to Burke (August 1990) provides a support undergarment with an abdominal support sling that connects to a dorsal panel. The nature of the connection is such that the sling could pivot to some extent, and therefore be positioned somewhat higher or lower on the abdomen as needed. Unfortunately, the mechanics is such that the weight carried by the sling passes through the pivot, so that the weight may well be improperly carried in all but the default position.

U.S. Pat. No. 4,557,268 to Maddux et al. (December 1985) provides front and back belts that connect at hook and loop type fasteners at the sides of the wearer. The connection in this instance provides some measure of independence in positioning between the front and back belts. There is an additional problem here with respect to use of the belts. The contemplated belts are substantially the same thickness across their entire lengths. If they are narrow enough to connect conveniently at the sides, then the belts are probably too narrow to comfortably support much abdominal weight. If they are wide enough to comfortably support additional considerable abdominal weight, then they would be cumbersome across the back, and in their connections to one another.

U.S. Pat. No. 4,108,149 to Castiglia (August 1978) provides a tall partially encircling, substantially rigid back brace portion, and a front portion that attaches to hook and loop fasteners on the front ends of the back portion. This device could be manipulated to provide higher or lower support as needed, but the use of a single front piece greatly limits the possible combinations.

Thus, there is a continuing need for a lower torso support in which the abdominal support portion is independently positionable relative to the back portion.

SUMMARY OF THE INVENTION

The present invention provides systems and methods in which a lower torso support has first and second front panels that are attachable to each other, and independently moveable with respect to the side portions of the support.

In the back, the left and right side portions can be connected to one another via a third piece, or more preferably comprise a single continuous piece of material. In the front, the ends of the side portions preferably overlap across the wearer's abdomen, and are connected by a hook and loop or other quick release mechanism.

Tightening of the support can be accomplished by any suitable mechanism. Particularly contemplated mechanisms use pull tabs that are operated by draw cables. One or more such cables can be used, and such cables preferably operate against pulleys or posts to provide mechanically advantaged tightening.

The front panels can be any suitable dimensions. However, slipper shapes are deemed to be the most useful. The front panels are preferably at least 15 cm long and at least 6 cm tall at their tallest point.

In preferred embodiments the front panels are independently (removing the panels without interfering with the coupling of the side portions) attachable to and detachable in any suitable orientation.

The front panels are also preferably coupleable to one another, which can again be advantageously accomplished using a hook and loop mechanism.

DETAILED DESCRIPTION

Figure 1:
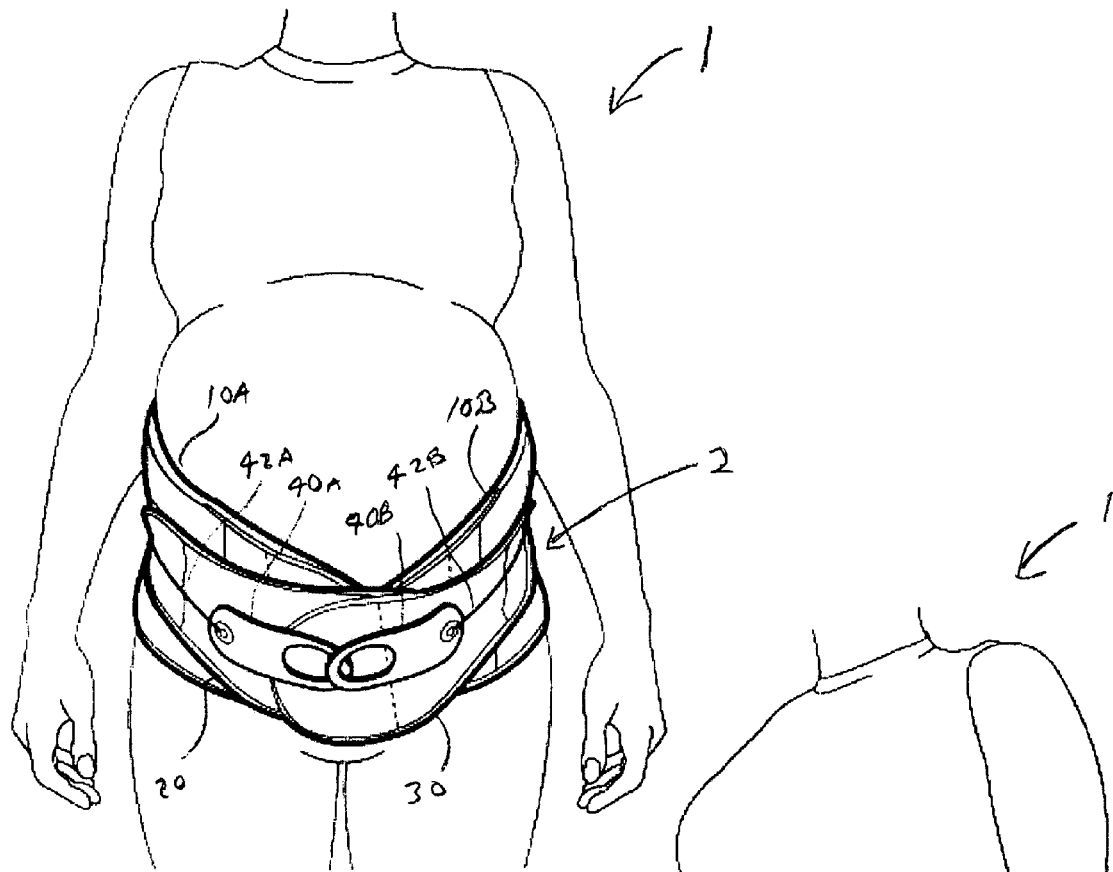
FIG. 1 is a front view of a woman wearing a support device according to the inventive subject matter.
Figure 2:
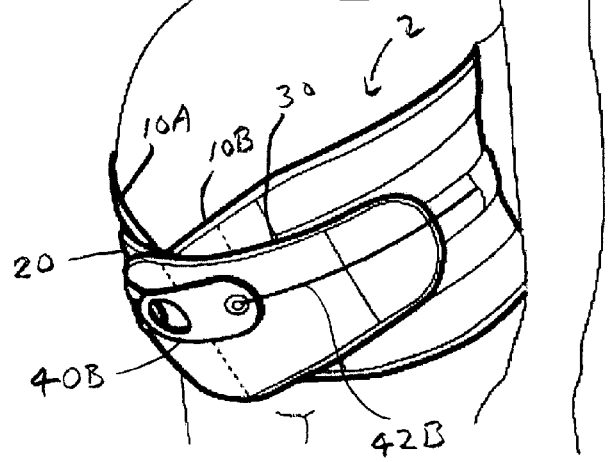
FIG. 2 is a left front perspective view of a woman wearing the support device of FIG. 1.

In FIGS. 1 and 2 a person 1 is wearing a support device 2, which generally comprises side portions 10A, 10B, front panels 20 and 30, and pull tabs 40A, 40B and draw cables 42A, 42B.

Except for the addition of the front panels 20 and 30, the support device 2 of FIGS. 1 and 2 is substantially the same as the Lumbar Back Brace With Mechanically Advantaged Draw Mechanism of pending PCT application serial no. PCT/US2004/16986, and/or the Double Pull Body Brace of pending U.S. application Ser. No. 10/440,525, both of which (as discussed above) are incorporated herein by reference in their entirety.

Thus, for example, the various dimensions, materials, and connections discussed in the PCT/US2004/16,986 and Ser. No. 10/440,525 applications are contemplated herein as well. In particular, tightening of the support about the lower torso can advantageously be accomplished via the pull tabs 40A, 40B and draw cables 42A, 42B as previously disclosed.

Similarly, the left and right side portions can be connected to one another via a third piece, or more preferably comprise a single continuous piece of material, as disclosed in PCT/US2004/16,986 and Ser. No. 10/440,525. In the front, the ends of the side portions 10A, 10B preferably overlap across the wearer's abdomen, and are connected by a hook and loop or other quick release mechanism (not shown).

Figure 3:
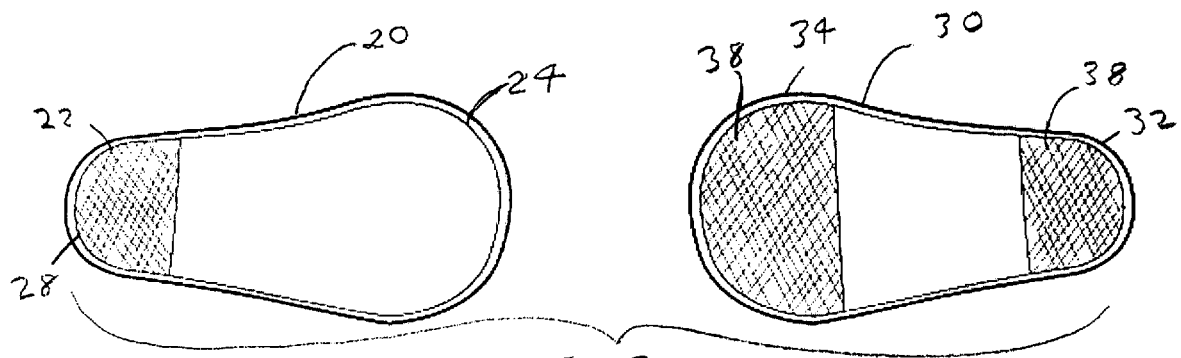
FIG. 3 is a bottom view of the right and left front panels of the support device of FIG. 1.
Figure 4:
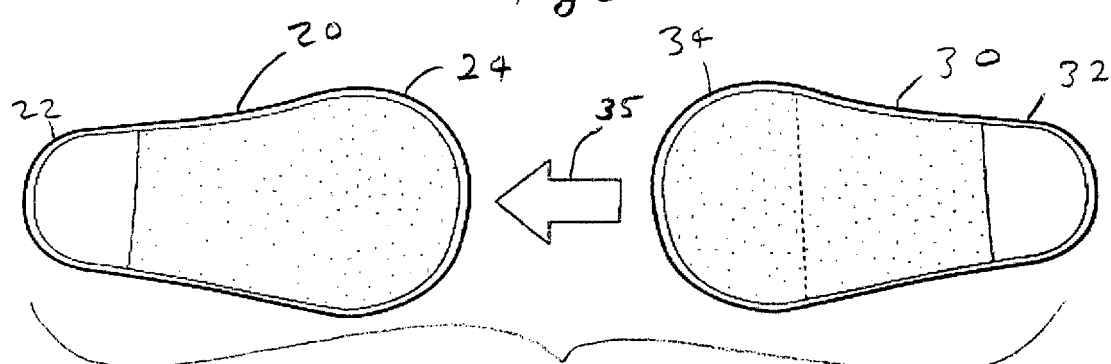
FIG. 4 is a top view of the right and left front panels of the support device of FIG. 1.
Figure 5:
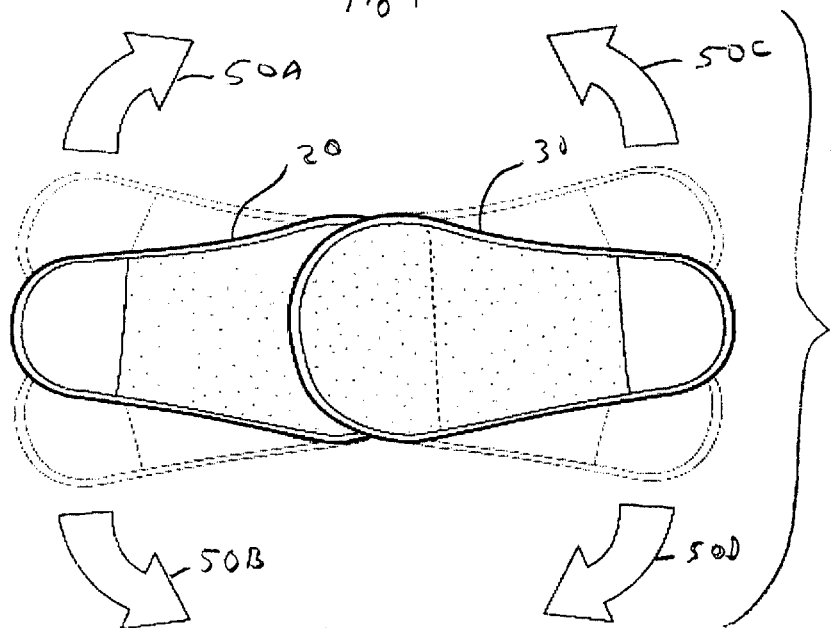
FIG. 5 is a front view of the right and left front panels of FIGS. 3, and 4, showing overlap of same.

The front panels 20 and 30 are best visualized in FIGS. 3, 4, and 5. In FIG. 3 the right front panel 20 generally comprises a slipper-shaped piece of strong but relatively pliable and soft fabric. Panel 20 has a heel end 22 and a toe end 24. The bottom side of the heel end 22 has a plurality of hooks 28 that cooperate with the a plurality of loops on the outside of the right side portion 10A of the device. Since the area of loops on the right side portion 10A is relatively large, front panel 20 can be moved superiorly or inferiorly (up or down), to the left or right (medially or laterally), and can be angled over perhaps a 90 degree span of angles on either side of horizontal.

Also in FIG. 3 the left front panel 30 generally comprises a similar slipper-shaped piece of strong but relatively pliable and soft fabric. Panel 30 also preferably has a heel end 32 and a toe end 34. The bottom side of the heel end 22 has a plurality of hooks 38 that cooperate with the a plurality of loops on the outside of the left side portion 10B of the device. Here again, the area of loops on the left side portion 10B is relatively large, so that front panel 30 can be moved in a great variety of positions and angles, independently of the positioning of the support device 2 on the wearer 1.

The bottom side of the toe end 22 also has a plurality of hooks 38, which cooperate with loops on the top of the toe end 24 of right front panel 20 to releasably couple the left front panel 30 to the right front panel 20.

In FIG. 4 the same front panels 20, 30 of FIG. 3 are depicted from the top view. At least in this embodiment, there are no hook areas visible from this view. It should nevertheless be appreciated that the top of toe portion 24 of the right front panel 20 includes a fabric that provides the loops for attachment by the bottom of toe portion 34 of left front panel 30. Arrow 35 depicts a potential movement of left front panels 30 so that its toe portion 34 overlaps the toe portion 24 of the right front panel 20.

The front panels can be any suitable dimensions. However, the inventors have put considerable research into advantages and disadvantages of possible shapes, and have concluded that a slipper shape is often the best design. Slipper shapes are somewhat elliptical, except that one of the ends (the toe end) is oversized, and one of the sides is relatively flat while the other is relatively curved. In that manner the panels appear to have handedness, or to continue the analogy, the overall shape of the panels would appear to fit a left or right foot better than the other foot. Research has also shown that the front panels should be at least 15 cm long and at least 6 cm tall at their tallest point. More preferably the front panels are at least 20 cm long and at least 8 cm tall at their tallest point.

Although the Figures show a preferred slipper shape for front panels 20, 30, it is contemplated that they could comprise other shapes. For example, alternative front panels should have a rectangular, teardrop, or elliptical shapes. They could even have a more whimsical shape, such as that of a left and right hands.

FIG. 5 shows how front panels 20, 30 can be oriented relative to each other, with a specific one of the almost unlimited number of alternatives shown in relief. Arrows 50A, 50B, 50C, and 50D show exemplary directions in which front panels 20, 30 can be moved. Note that as long as front panels 20, 30 are hooked together they can only move as a unit. To re-orient them relative to one another, the connection must be interrupted. Similarly, once the front panels 20, 30 are attached to their respective side portions 10A, 10B, their orientations are fixed with respect to the main body of the device, and cannot be re-oriented in that respect without interrupting those connections.

Thus, specific embodiments and applications of lumbar support with supplemental abdominal support panels have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. An abdominal support, comprising:
   left and right side portions coupled together across the patient's dorsal midline;
   first and second front panels that are independently attachable to and detachable from the side portions at substantially any desired angle to each other and to the side portions,
   and do not extend across the patient's dorsal spine.

2. The support of claim 1, wherein the left and right side portions comprise a single continuous piece of material.

3. The support of claim 1, further comprising pull tabs that overlay the front panels.

4. The support of claim 1, wherein one of the left and right side portions overlaps the other across the abdomen of the wearer.

5. The support of claim 4, wherein the left and right sides attach to each other using a hook and loop mechanism.

6. The support of claim 1, further comprising a first pull tab that draws a first cable to tighten the support around the lower torso of the wearer.

7. The support of claim 6, wherein the a cable cooperates with a mechanically advantageous mechanism to tighten the support around the lower torso of the wearer.

8. The support of claim 6, further comprising a second pull tab and a second cable that cooperate with the first pull tab and cable to tighten the support around the lower torso of the wearer.

9. The support of claim 1, further comprising a hook and loop mechanism that couples the left and right side portions across the wearer's ventral midline independently of any connection between the first and second front panels.

10. The support of claim 1, wherein the first and second front panels are completely removable by the wearer from the side portions without damaging the any of the front or side panels.

11. The support of claim 1, wherein the first front panel has an elongated overall shape with two ends, and is wider towards one end than towards the other end.

12. The support of claim 1, wherein the first front panel is substantially slipper shaped.

13. The support of claim 1, wherein the first front panel is at least 15 cm long.

14. The support of claim 1, wherein the first front panel is at least 6 cm tall at its tallest point.

15. The support of claim 1, wherein the first front panel is at least 15 cm long, and at least 6 cm tall at its tallest point.

16. The support of claim 1, further comprising a hook and loop mechanism that couples the first and second front panels to the left and right side portions, respectively.

17. The support of claim 1, further comprising a hook and loop mechanism that couples the first and second front panels to one another.

18. The support of claim 1, further comprising a hook and loop mechanism that couples the first and second front panels to the left and right side portions, respectively, and that couples the first and second front panels to one another.

19. The support of claim 1, wherein the panels are adjustably movable angularly, superiorly, inferiorly, medially, laterally, or a combination of these directions independent of the side portions.

20. An abdominal support, comprising:
  left and right side portions that can overlap one another across a wearer's abdomen;
  first and second front panels attachable to outer sides of the side portions and to one another across the wearer's abdomen; and
  wherein the first and second front panels can be independently attached to and detached from the side portions at sunbstantially any desired angle to each other and to the side portions, respectively.

* * * * *